(12) United States Patent
Peitz et al.

(10) Patent No.: US 11,021,417 B2
(45) Date of Patent: Jun. 1, 2021

(54) PROCESS FOR OLIGOMERIZATION WITH DRY HANDLING OF A CATALYST BEFORE CHARGING TO THE REACTOR

(71) Applicant: Evonik Operations GmbH, Essen (DE)

(72) Inventors: Stephan Peitz, Oer-Erkenschwick (DE); Guido Stochniol, Haltern am See (DE); Reiner Bukohl, Marl (DE)

(73) Assignee: Evonik Operations GmbH, Essen (DE)

( * ) Notice: Subject to any disclaimer, the term of this patent is extended or adjusted under 35 U.S.C. 154(b) by 34 days.

(21) Appl. No.: 16/710,784

(22) Filed: Dec. 11, 2019

(65) Prior Publication Data

US 2020/0189992 A1 Jun. 18, 2020

(30) Foreign Application Priority Data

Dec. 13, 2018 (EP) ..................................... 18212259

(51) Int. Cl.
*C07C 2/10* (2006.01)
*B01J 38/02* (2006.01)

(52) U.S. Cl.
CPC .................. *C07C 2/10* (2013.01); *B01J 38/02* (2013.01); *C07C 2521/12* (2013.01); *C07C 2523/755* (2013.01); *C07C 2529/06* (2013.01)

(58) Field of Classification Search
None
See application file for complete search history.

(56) References Cited

U.S. PATENT DOCUMENTS

| 8,779,228 | B2 | 7/2014 | Heidemann et al. |
| 2011/0301398 | A1* | 12/2011 | Heidemann ............ C10G 50/00 585/512 |
| 2016/0152527 | A1* | 6/2016 | Peitz ..................... C07C 45/505 549/313 |

FOREIGN PATENT DOCUMENTS

| EP | 0 329 305 | 8/1989 |
| WO | 2010/057905 | 5/2010 |

OTHER PUBLICATIONS

U.S. Appl. No. 16/711,012, filed Dec. 11, 2019, Stephan Peitz et al.
European Search Report dated Jun. 4, 2019 in European Application 18212259.8.

* cited by examiner

*Primary Examiner* — Ali Z Fadhel
(74) *Attorney, Agent, or Firm* — Grüneberg and Myers PLLC

(57) ABSTRACT

A process is useful for the oligomerization of short-chain olefins in the presence of a catalyst, wherein the catalyst is kept in a dry atmosphere prior to being used in the process.

16 Claims, No Drawings

PROCESS FOR OLIGOMERIZATION WITH DRY HANDLING OF A CATALYST BEFORE CHARGING TO THE REACTOR

CROSS-REFERENCE TO A RELATED APPLICATION

The present application claims the benefit to the European application EP 18212259.8, filed on Dec. 13, 2018, which is incorporated by reference in its entirety.

BACKGROUND OF THE INVENTION

Field of the Invention

The present invention relates to a process for the oligomerization of short-chain olefins in the presence of a catalyst, wherein the catalyst is kept in a dry atmosphere prior to being used in the process.

Discussion of the Background

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Processes for oligomerizing olefins are sufficiently well known in the related art and are used on an industrial scale. The production quantities amount to several thousand metric kilotons per year in Germany alone. The catalysts used in the oligomerization of olefins have high activities and are sometimes adjusted precisely to the particular oligomerization process.

The first charging of the reactor with the oligomerization catalyst or the replacement of the existing catalyst is carried out typically under standard ambient conditions of pressure (approximately 1013 mbar), temperature (external temperature, approximately 0 to 40° C.) and humidity (on average >70%). Standard ambient conditions also typically prevail during the storage and the transport of the catalyst from the place of production to the reactor as the place of use. After the reactor has been charged with the oligomerization catalyst, the reactor is started up, i.e. the space velocity of the feedstock mixture for oligomerization over the catalyst is slowly increased.

The problem here is that even with full space velocity over the catalyst, it may take several days or weeks until a desired target conversion in the oligomerization can be achieved with the newly installed or replaced oligomerization catalyst.

SUMMARY OF THE INVENTION

The object of the present invention was to provide a process with which the start-up time of the oligomerization catalyst can be reduced. The basic object of the present invention was achieved with the process for oligomerization according to embodiment 1 and with the process for exchanging an oligomerization catalyst according to embodiment 13. Preferred configurations are specified in further embodiments below.

1. Process for the oligomerization of $C_3$- to $C_6$-olefins, the oligomerization taking place in at least one reaction stage, which consists in each case of at least one reactor and at least one distillation column, using an oligomerization catalyst, characterized in that the oligomerization catalyst before being charged to the reaction stage in storage, transport and/or in charging to the reaction stage is kept in a dry atmosphere at less than 65% relative humidity.
2. Process for the oligomerization according to embodiment 1, wherein the fresh oligomerization catalyst in storage, transport and/or charging to the reaction stage is kept in a dry atmosphere at less than 60% relative humidity.
3. Process for the oligomerization according to embodiment 1, wherein the fresh oligomerization catalyst in storage, transport and/or charging to the reaction stage is kept in a dry atmosphere at less than 50% relative humidity.
4. Process for the oligomerization according to any of embodiments 1 to 3, wherein the oligomerization catalyst before being charged to the reaction stage in storage, transport and/or in charging to the reaction stage is kept in a dry atmosphere whose humidity is lower by at least 3% than the humidity of the surroundings.
5. Process for the oligomerization according to any of embodiments 1 to 4, wherein the oligomerization catalyst in the first reaction stage is selected from heterogeneous transition-metal-containing oligomerization catalysts, the transition metal being nickel, cobalt, chromium, titanium or tantalum.
6. Process for the oligomerization according to any of embodiments 1 to 5, wherein the oligomerization catalyst in the second reaction stage is selected from heterogeneous transition-metal-containing oligomerization catalysts, the transition metal being nickel, cobalt, chromium, titanium or tantalum.
7. Process for the oligomerization according to any of embodiments 1 to 6, wherein the oligomerization catalyst of the first reaction stage and the oligomerization catalyst of the second reaction stage each independently comprises or consists of a nickel compound on an aluminosilicate support material.
8. Process according to embodiment 7, wherein the oligomerization catalyst has a composition of 15 to 40% by weight of NiO, 5 to 30% by weight of $Al_2O_3$, 55 to 80% by weight of $SiO_2$ and 0.01 to 2.5% by weight of an alkali metal oxide.
9. Process for the oligomerization according to any of embodiments 1 to 8, wherein the process comprises two, three, four or five reaction stages.
10. Process for the oligomerization according to any of embodiments 1 to 9, wherein the oligomerization catalyst used for charging is a newly produced oligomerization catalyst or a regenerated oligomerization catalyst.
11. Process for the oligomerization according to embodiment 10, wherein the regenerated oligomerization catalyst is produced by the steps A) of burning off an oligomerization catalyst used for the oligomerization and B) of impregnating the oligomerization catalyst burnt off in step A) with a solution of a transition metal compound and subsequent calcining.

12. Process for the oligomerization according to any of embodiments 1 to 11, wherein the oligomerization is carried out at a temperature in the range of 50 to 200° C. and at a pressure of 10 to 70 bar.

13. Process for the replacement of an oligomerization catalyst with a fresh oligomerization catalyst in a reaction stage, characterized in that before the replacement in storage, transport and/or during the replacement on charging to the reaction stage, the fresh oligomerization catalyst used for the replacement is kept in a dry atmosphere at less than 65% relative humidity.

14. Process for the replacement of an oligomerization catalyst according to embodiment 13, wherein before the replacement in storage, transport and/or during the replacement on charging to the reaction stage, the fresh oligomerization catalyst used for the replacement is kept in a dry atmosphere at less than 60% relative humidity.

15. Process for the replacement of an oligomerization catalyst according to embodiment 13, wherein before the replacement in storage, transport and/or during the replacement on charging to the reaction stage, the fresh oligomerization catalyst used for the replacement is kept in a dry atmosphere whose humidity is lower by at least 3% than the humidity of the surroundings.

DETAILED DESCRIPTION OF THE INVENTION

The process according to the invention is a process for oligomerization of $C_3$- to $C_6$-olefins, the oligomerization taking place in at least one reaction stage, which consists in each case of at least one reactor and at least one distillation column, using an oligomerization catalyst, characterized in that the oligomerization catalyst before being charged to the reaction stage in storage, transport and/or in charging to the reaction stage is kept in a dry atmosphere at less than 65% relative humidity.

In the context of the present invention, the term "reaction stage" encompasses a unit composed of one or more reactors and of one or more distillation columns. In the distillation columns, the remaining starting mixture comprising, for example, alkanes and unreacted olefins, are separated in particular from the product oligomers generated. Typical process-engineering ancillary units which can be incorporated in the reaction stages, such as preheaters for the feed, heat exchangers or similar, are not listed separately here but are familiar to those skilled in the art.

With the process of the invention it has surprisingly emerged that if when handling the oligomerization catalyst, i.e. when storing it or transporting it before it is charged to the reaction stage and/or when it is charged to the reaction stage, a dry atmosphere is ensured, i.e. a relative humidity of less than 65%, preferably of less than 60%, particularly preferably of less than 50?, it is possible to achieve a reduced start-up time of the catalyst after charging to the reactor.

In one preferred embodiment of the present invention, the oligomerization catalyst before being charged to the reaction stage in storage, transport and/or in charging to the reaction stage is kept in a dry atmosphere whose humidity is lower by at least 3%, preferably by at least 5%, particularly preferably by at least 10% than the humidity of the surroundings. By surroundings in the sense of the present invention are meant the humidity in the geographic region in which the oligomerization catalyst is being handled.

Oligomerization catalysts are typically not produced directly in the reactor. Therefore, the freshly produced oligomerization catalysts must first be stored before they are transported to the plant and charged to a reaction stage. Charging to the reaction stage refers in particular to their charging into the one or more reactors of the respective reaction stage. The process of the invention relates to all charging procedures of a reaction stage in the context of the oligomerization—in other words, the first-time filling of a reaction stage or a reactor, and the replacement of an existing "spent" oligomerization catalyst with a fresh oligomerization catalyst. In the context of the present invention, the term fresh oligomerization catalyst means both newly produced catalysts and regenerated catalysts, which have already been used in a reactor for oligomerization, after removal but which have been regenerated by the method described below.

The procedure claimed allows the desired conversion to be attained after just a few hours. In contrast, a catalyst which has been stored, transported and/or charged at a humidity of more than 65% and/or, preferably, which has been stored, transported and/or charged at a humidity which is lower by less than 3% than the humidity of the surroundings may require several days or even a few weeks to achieve the desired target conversion.

The process according to the invention is carried out broadly as follows. The starting point is a process for oligomerizing olefins in one or more, i.e. at least two, reaction stages. The catalyst used for the oligomerization is kept at a humidity of less than 65% after production and before charging to the reactor or reactors, in storage, transport and/or in charging to the reactor or reactors.

After a period of 3 to 6 years, there is a decline in catalyst activity, owing to occlusion and/or poisoning of the active centres, and the oligomerization catalyst must be replaced. For this purpose, the feedstock mixture containing the olefins to be oligomerized is shut off or fed to a different reaction stage. The oligomerization catalyst can be withdrawn from the reactor or reactors that are now no longer being charged with olefins. For this removal, the reactor or reactors of the bypassed reaction stage are firstly purged with an inert gas in order to remove volatile organic substances. The reactor or reactors are then opened and the catalyst is withdrawn. As soon as the oligomerization catalyst has been removed from the reactor or reactors, it or they are filled with a fresh catalyst under the conditions claimed. Thereafter the reactor or reactors are inertized to prevent oxygen in the reactor, and are started up and so transferred to operation.

The process according to the invention comprises at least one reaction stage. In a preferred embodiment, the process for oligomerization comprises at maximum five reaction stages. Particularly preferred is a process regime with two, three, four or five reaction stages. Each of these reaction stages, independently of one another, comprises one or more reactors and one or more distillation columns in order to separate the oligomers formed from the residual starting mixture. It is also conceivable, however, that one of the reaction stages comprises two or more reactors, whereas in a preceding or subsequent reaction stage only one reactor is present.

Olefins employable for the process according to the invention are $C_3$- to $C_6$-olefins, preferably $C_3$- to $C_5$-olefins, particularly preferably $C_4$-olefins, or olefin mixtures based thereon which may also comprise proportions of analogous alkanes. Suitable olefins are, inter alia, α-olefins, n-olefins and cycloalkenes, preferably n-olefins. In a preferred embodiment, the olefin is n-butene.

The olefins are typically not used as reactants in pure form, but in available technical-grade mixtures. The term starting mixture used additionally in this invention is therefore to be understood as encompassing any type of mixtures containing the relevant olefins to be oligomerized in an amount which makes it possible to perform the oligomerization economically. The starting mixtures used in accordance with the invention preferably contain practically no further unsaturated compounds and polyunsaturated compounds such as dienes or acetylene derivatives. It is preferable to employ starting mixtures containing less than 5% by weight, in particular less than 2% by weight, of branched olefins based on the olefin proportion.

Propylene is produced on a large industrial scale by cracking of naphtha and is a commodity chemical which is readily available. $C_5$-olefins are present in light petroleum fractions from refineries or crackers. Technical mixtures which comprise linear $C_4$ olefins are light petroleum fractions from refineries, $C_4$ fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the $C_4$-fraction of a steam cracker. Butadiene is removed in the first step here. This is accomplished either by extraction (distillation) of the butadiene or by selective hydrogenation thereof. In both cases a virtually butadiene-free $C_4$-cut is obtained, the so-called raffinate I. In the second step, isobutene is removed from the $C_4$-stream, for example by production of MTBE by reaction with methanol. The now isobutene-free and butadiene-free $C_4$-cut, the so-called raffinate II, contains the linear butenes and any butanes. If at least some of the 1-butene obtained is removed therefrom, the so-called raffinate III is obtained.

In a preferred embodiment in the process according to the invention, $C_4$-olefin-containing streams are fed as starting mixture. Suitable olefin mixtures are particularly raffinate I and raffinate II and raffinate III.

The reactor or reactors in the respective reaction stage(s) each comprise an oligomerization catalyst, in particular a heterogeneous oligomerization catalyst. The oligomerization catalyst in this case is particularly in the form of granules, an extrudate or in tablet form.

The (heterogeneous) oligomerization catalysts in the individual reactors of the one or more reaction stage(s) may in each case be independently selected from transition-metal-containing oligomerization catalysts. The transition metals or transition metal compounds employed correspondingly are preferably at this stage on a support material, preferably an aluminosilicate-based support material. Transition metal compounds especially suitable for the oligomerization catalysts used according to the invention are compounds of nickel, cobalt, chromium, titanium and tantalum. Nickel compounds and cobalt compounds are preferred, nickel compounds being particularly preferred.

In a preferred embodiment, the oligomerization catalyst according to the invention comprises a nickel compound, preferably nickel oxide, on an aluminosilicate support material. The support material can be an amorphous, mesoporous aluminosilicate, a crystalline, microporous aluminosilicate or an aluminosilicate having amorphous and crystalline phases. In the context of the present invention "amorphous" is to be understood as meaning the property of a solid which results from the fact that the solid has no crystal structure, i.e. no long-range order. However, it cannot be ruled out in the context of the present invention that the amorphous silica-alumina support material has small crystalline domains.

According to the invention, the oligomerization catalyst preferably has a composition of 15% to 40%/h by weight, preferably 15% to 30% by weight NiO, 5% to 30% by weight $Al_2O_3$, 55% to 80% by weight $SiO_2$ and 0.01% to 2.5% by weight, preferably 0.05% to 2% by weight, of an alkali metal oxide, preferably sodium oxide. The figures are based on a total composition of 100% by weight. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition.

The oligomerization catalyst preferably leas a specific surface area (calculated according to BET) of 150 to 700 $m^2/g$, more preferably 190 to 600 $m^2/g$, particularly preferably 220 to 550 $m^2/g$. The BET surface area is measured by nitrogen physisorption according to DIN ISO 9277 (2014-01 version).

The oligomerization catalysts present in the individual reactors in the reaction stages) may be selected in each case independently of one another from the aforementioned substances. The individual oligomerization catalysts in the reactors are not always exactly identical here, but differ from each other in the composition, possibly only to a limited extent. This is also due to the fact that even if at the time point of the first start-up of the process according to the invention each reactor contains a fully identical catalyst composition, this composition changes with time during operation by the widest variety of effects over the course of the years (regenerated catalysts behave differently to freshly produced catalysts, abrasion during operation, different ageing rates and/or poisoning, etc.).

A reduction in conversion and/or selectivity (generally catalyst activity) during oligomerization due to ageing and/or poisoning may be encountered with increasing employment time f the oligomerization catalyst. The catalyst according to the invention is then exchanged and is replaced by a fresh oligomerization catalyst, i.e. a new or a regenerated oligomerization catalyst.

An oligomerization catalyst can be produced by the known processes of impregnation, wherein the support material is charged with a solution of a transition metal compound, especially a nickel compound, and is then calcined, or coprecipitation in which the entire catalyst composition is precipitated from a single, mostly aqueous solution. The oligomerization catalyst can also be produced by other processes familiar to those skilled in the art.

After use of the produced oligomerization catalyst in the oligomerization, the catalyst can also be regenerated in order to increase again the catalyst activity (for the oligomerization). The regeneration of the oligomerization catalyst in particular comprises the step A) of burning off and B) of the impregnation with a solution of a transition metal compound. In this case, the transition metal in the catalyst to be regenerated and the transition metal in the impregnation solution should be identical.

After use in oligomerization, the oligomerization catalyst may exhibit deposits of organic substances that require removal. Removal of the organic compounds deposited in the catalyst is preferably accomplished in step A) by simple burning off to form carbon oxides and water. The burnoff in step A) may be carried out continuously or discontinuously in a furnace, for example in a rotary kiln or a shaft furnace. For this purpose the oligomerization catalyst (for example in the form of a granulate) is supplied to the furnace and preferably burnt off at a furnace temperature of 400° C. to 600° C., particularly preferably of 500° C. to 600° C. The burnoff can be carried out using additionally supplied combustion air. This combustion air can be supplied in countercurrent and in addition further air is optionally blown into the oligomerization catalyst via suitable inlets to ensure rapid burnoff.

Step B) comprises treating/impregnating the oligomerization catalyst burnt off in step A) with a solution of a transition metal compound, in particular a solution of a nickel compound, as step B1), and calcination of the treated oligomerization catalyst as step B2).

The performance of step B1) of the regeneration, in this example by nickel, is discussed below. However, the statements are also applicable to other transition metals.

The impregnation with nickel in step B1) may be effected similarly to the production of the oligomerization catalyst but optionally with the difference that a nickel solution having a lower nickel concentration than in the production of the oligomerization catalyst may be used. In principle any soluble nickel compound such as nickel nitrate ($Ni(NO_3)_2$), nickel acetate ($Ni(ac)_2$), nickel acetylacetonate ($Ni(acac)_2$), nickel sulfate ($NiSO_4$) or nickel carbonate ($NiCO_3$) may be used therefor to produce an aqueous or ammoniacal nickel solution.

The use of NiHAC solutions obtainable by dissolving nickel carbonate ($NiCO_3$) in concentrated ammonia solutions, optionally with addition of ammonium carbonate, has proven particularly advantageous. Such solutions may be used for the impregnation with nickel contents of 0.5 to 14% by weight, in particular of 2 to 10% by weight, especially preferably of 4 to 8% by weight.

For nickel application the oligomerization catalyst burned off in step A) is, for example, impregnated with a NiHAC solution having nickel contents of 0.5 to 14% by weight, in particular of 2% to 10% by weight, very particularly of 4% to 8% by weight until saturation of the pores present in the oligomerization catalyst. The impregnation may be performed with a process familiar to those skilled in the art such as for example by spraying until permanent appearance of a liquid film on the surface (incipient wetness). If the solution takeup is about 0.8 to 1.2 g of solution per g of oligomerization catalyst a deposition of about 0.5% to 6% by weight of additional nickel in the form of a basic carbonate can be achieved.

After step B1), the impregnated oligomerization catalyst can be dried in a suitable drying apparatus, for example a belt dryer with an air stream or else a conical dryer, at temperatures between 100° C. and 250° C., preferably between 120° C. and 220° C., and at standard pressure or else under vacuum, before calcination is conducted in step B2). By means of drying, water or excess ammonia in particular is discharged from the NiHAC solution.

The calcination of the oligomerization catalyst in step B2) may be carried out continuously or discontinuously in a suitable furnace, for example a shaft furnace or rotary kiln. In the case of continuous calcination, it is furthermore preferable when a gas is passed in countercurrent through the oligomerization catalyst, particularly in the form of a granulate. The gas employed may be air, nitrogen or a mixture thereof. The gas stream may be 0.2 to 4 m³ of gas per kg of granulate per hour and the inlet temperature of the gas may be from 400° C. to 800° C. preferably 450° C. to 700° C. In addition to this heat introduced via the gas, energy may be introduced by active heating of the walls of the furnace.

The calcination temperature in the furnace in step B2) may be 400° C. to 800° C., preferably 450° C. to 700° C., particularly preferably 500° C. to 600° C. This temperature may be maintained over several hours, preferably 5 to 60 hours, particularly preferably 10 to 40 hours, before the catalyst is cooled. Cooling is preferably carried out in a nitrogen stream. Air may additionally be added to the nitrogen and the amount of air should preferably be controlled. The amount of air preferably added to the nitrogen may be 100 to 10 000 ppm by volume, preferably 300 to 7000 ppm by volume.

The oligomerization of the process according to the invention can be carried out at a temperature in the range from 50° C. to 200° C., by preference 60° C. to 180° C., preferably in the range from 60° C. to 130° C., and at a pressure of 10 to 70 bar, preferably of 20 to 55 bar. In a preferred embodiment of the present invention, the oligomerization is carried out in the liquid phase. If the oligomerization is to be carried out in the liquid phase the parameters pressure and temperature must to this end be chosen such that the reactant stream (the employed olefins or olefin mixtures) is in the liquid phase.

The weight-based space velocities (reactant mass per unit catalyst mass per unit time; weight hourly space velocity (WHSV)) are in the range between 1 g of reactant per g of catalyst and per h (=1 h⁻¹) and 190 h⁻¹, preferably between 2 h⁻¹ and 35 h⁻¹, in particular preferably between 3 h⁻¹ and 25 h⁻¹.

In one embodiment, particularly when using a catalyst comprising a nickel compound, preferably nickel oxide, on an aluminosilicate support, the degree of dimerization (also referred to as "percentage selectivity based on dimerization") after the oligomerization, based on the converted reactant, is at least 60%, more preferably at least 75%, particularly preferably at least 80%.

The linearity of an oligomerization product or of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a $C_8$ fraction. The lower the ISO index, the more linear the construction of the molecules in the respective fraction. The ISO index is calculated according to the following general formula:

$$\frac{(\text{single-branched dimers (wt \%)} + 2 \times \text{double-branched dimers (wt \%)})}{100}$$

Accordingly, a dimer mixture having an ISO index of 1.0 has an average of exactly one methyl branch per dimeric molecule.

The ISO index of the product from the oligomerization process according to the invention preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a notional mixture by hydroformylation. This provides either the corresponding carboxylic acids by oxidation or a $C_9$-alcohol mixture by hydrogenation. The $C_9$ acid mixture may be used for producing lubricants or siccatives. The $C_9$-alcohol mixture is a precursor for the production of plasticizers, particularly dinonyl phthalates, or Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

EXAMPLES

The present invention is more particularly elucidated hereinbelow with reference to examples. Alternative embodiments of the present invention are obtainable analogously.

Example 1 (Inventive)

A nickel (oxide)-containing aluminosilicate catalyst with 20% by weight of nickel, after production and before charging to the reactor, was stored for three months in a vessel with airtight sealing. Before being charged to the reactor, it was kept in ambient air at 50% relative humidity for 24 hours. The reactor was operated at 80° C. and 30 bar with a mass flow rate of 1 kg/h of $C_4$ mixture; the butene content was 72%. In addition to this fresh feed, 1 kg/h of reactor discharge was recycled, and so the total feed was 2 kg/h. After a running time of 6 hours, the conversion of butenes reached a constant level of 49%. After raising of the reaction temperature to 90° C., the conversion was 50.5%.

Example 2 (Non-Inventive)

An oligomerization catalyst (same catalyst as in Example 1) was stored after production for three months in a vessel with airtight sealing. Before being charged to the reactor, it was kept in ambient air at 95% relative humidity for 24 hours. The reactor was operated at 90° C. and 30 bar with a mass flow rate of 1 kg/h of $C_4$ mixture; the butene content was 75%. In addition to this fresh feed, 1 kg/h of reactor discharge was recycled, and so the total feed was 2 kg/h. After a running time of 46 hours, a conversion of 35% was reached. Only after a running time of 140 hours did the conversion of butenes reach a constant level of 50.5%.

Example 3 (Non-Inventive)

An oligomerization catalyst (same catalyst as in Example 1) was stored after production for three months in a vessel with airtight sealing. Before being charged to the reactor, it was kept in ambient air at 95% relative humidity for 4.5 weeks. The reactor was operated at 90° C. and 30 bar with a mass flow rate of 1 kg/h of $C_4$ mixture; the butene content was 75%. In addition to this fresh feed, 1 kg/h of reactor discharge was recycled, and so the total feed was 2 kg/ft. A conversion of 1% was achieved after a running time of 436 hours and of 26.4% after 555 h. After a running time of 795 hours, the conversion of butenes reached a constant level of 39%.

The experiments show clearly that storage in air at high humidity leads to problems during start-up, and sufficient conversions, as in the case of the inventive example, are completely unachievable or can only be achieved after long times of deployment.

The invention claimed is:

1. A process for oligomerization of $C_3$- to $C_6$-olefins, the process comprising:
   reacting a $C_3$- to $C_6$-olefin in at least one reaction stage, which comprises in each case at least one reactor and at least one distillation column,
   wherein the oligomerization is catalysed with an oligomerization catalyst,
   wherein the oligomerization catalyst, before being charged to the reaction stage, in storage, transport, and/or in charging to the reaction stage, is kept in a dry atmosphere at less than 65% relative humidity, and
   wherein the oligomerization catalyst has a composition of:
   15 to 40% by weight of NiO,
   5 to 30% by weight of $Al_2O_3$,
   55 to 80% by weight of $SiO_2$, and
   0.01 to 2.5% by weight of an alkali metal oxide.

2. The process according to claim 1, wherein the oligomerization catalyst in storage, transport and/or charging to the reaction stage, is kept in a dry atmosphere at less than 60% relative humidity.

3. The process according to claim 1, wherein the oligomerization catalyst in storage, transport and/or charging to the reaction stage, is kept in a dry atmosphere at less than 50% relative humidity.

4. The process according to claim 1, wherein the oligomerization catalyst, before being charged to the reaction stage in storage, transport and/or in charging to the reaction stage, is kept in a dry atmosphere where humidity is lower by at least 3% than the humidity of the surroundings.

5. The process for the oligomerization according to claim 1, further comprising a second reaction stage, wherein the oligomerization catalyst in the second reaction stage is selected from heterogeneous transition-metal-containing oligomerization catalysts, wherein the transition metal is selected from the group consisting of nickel, cobalt, chromium, titanium and tantalum.

6. The process according to claim 5, wherein the oligomerization catalyst of the second reaction stage comprises or consists of a nickel compound on an aluminosilicate support material.

7. The process according to claim 6, wherein both of the oligomerization catalysts have a composition of:
   15 to 40% by weight of NiO,
   5 to 30% by weight of $Al_2O_3$,
   55 to 80% by weight of $SiO_2$, and
   0.01 to 2.5% by weight of an alkali metal oxide.

8. The process according to claim 1, wherein the process comprises two, three, four or five reaction stages.

9. The process according to claim 1, wherein the oligomerization catalyst used for charging is a newly produced oligomerization catalyst or a regenerated oligomerization catalyst.

10. The process according to claim 9, wherein the oligomerization catalyst used for charging is the regenerated oligomerization catalyst, and wherein the regenerated oligomerization catalyst is produced by:
    A) burning off an oligomerization catalyst used for the oligomerization, and
    B) impregnating the oligomerization catalyst burnt off in A) with a solution of a transition metal compound and subsequent calcining.

11. The process according to claim 1, wherein the oligomerization is carried out at a temperature in the range of 50 to 200° C. and at a pressure of 10 to 70 bar.

12. A process for replacement of an oligomerization catalyst with a fresh oligomerization catalyst in a reaction stage, the process comprising:
keeping the fresh oligomerization catalyst in a dry atmosphere at less than 65% relative humidity, before replacement in storage, transport and/or during replacement on charging to a reaction stage,
wherein the fresh oligomerization catalyst has a composition of:
15 to 40% by weight of NiO,
5 to 30% by weight of $Al_2O_3$,
55 to 80% by weight of Sift, and
0.01 to 2.5% by weight of an alkali metal oxide.

13. The process according to claim 1, further comprising producing an aldehyde, alcohol, or carboxylic acid from the oligomers produced in claim 1.

14. The process according to claim 12, wherein before the replacement in storage, transport and/or during the replacement on charging to the reaction stage, the fresh oligomerization catalyst used for the replacement is kept in a dry atmosphere at less than 60% relative humidity.

15. The process according to claim 12, wherein before the replacement in storage, transport and/or during the replacement on charging to the reaction stage, the fresh oligomerization catalyst used for the replacement is kept in a dry atmosphere where humidity is lower by at least 3% than the humidity of the surroundings.

16. An oligomerization system for $C_3$- to $C_6$-olefins, the system comprising:
at least one reaction stage, wherein the at least one reaction stage comprises at least one reaction and at least one distillation column,
an oligomerization catalyst, wherein the oligomerization catalyst, before being charged to the at least one reaction stage in storage, transport, and/or in charging to the at least one reaction stage, is kept in a dry atmosphere at less than 65% relative humidity, and
a fresh oligomerization catalyst kept in a dry atmosphere at less than 65% relative humidity,
wherein the oligomerization catalyst has a composition of:
15 to 40% by weight of NiO,
5 to 30% by weight of $Al_2O_3$,
55 to 80% by weight of $SiO_2$, and
0.01 to 2.5% by weight of an alkali metal oxide.

* * * * *